US010527612B2

(12) United States Patent
Lin et al.

(10) Patent No.: US 10,527,612 B2
(45) Date of Patent: Jan. 7, 2020

(54) METHOD AND ARRANGEMENT FOR DETECTING BINDING EVENTS OF MOLECULES

(71) Applicant: Technische Universitaet Dresden, Dresden (DE)

(72) Inventors: Weilin Lin, Dresden (DE); Robert Wieduwild, Dresden (DE); Luca Mannocci, Eiken (CH); Jana Herrmann, Dresden (DE); Yixin Zhang, Dresden (DE); Francesco Reddavide, Dresden (DE)

(73) Assignee: TECHNISCHE UNIVERSITAET DRESDEN, Dresden (DE)

( * ) Notice: Subject to any disclaimer, the term of this patent is extended or adjusted under 35 U.S.C. 154(b) by 398 days.

(21) Appl. No.: 14/902,437

(22) PCT Filed: Jul. 2, 2014

(86) PCT No.: PCT/EP2014/064097
§ 371 (c)(1),
(2) Date: Dec. 31, 2015

(87) PCT Pub. No.: WO2015/000978
PCT Pub. Date: Jan. 8, 2015

(65) Prior Publication Data
US 2016/0377608 A1 Dec. 29, 2016

(30) Foreign Application Priority Data

Jul. 2, 2013 (DE) .................. 10 2013 011 304

(51) Int. Cl.
C07H 21/02 (2006.01)
G01N 33/543 (2006.01)
C12Q 1/6837 (2018.01)

(52) U.S. Cl.
CPC ..... *G01N 33/54306* (2013.01); *C12Q 1/6837* (2013.01); *G01N 33/54353* (2013.01); *G01N 33/54393* (2013.01)

(58) Field of Classification Search
USPC ......... 435/6.1, 6.11, 91.1, 183; 436/94, 501; 536/23.1, 24.3, 24.33
See application file for complete search history.

(56) References Cited

U.S. PATENT DOCUMENTS

2003/0162185 A1\* 8/2003 Melnyk .................. C07H 21/00
435/6.16
2003/0224377 A1\* 12/2003 Wengel .................. C07H 19/04
435/6.12

(Continued)

FOREIGN PATENT DOCUMENTS

DE  10 2006057975 A1  6/2007
JP     2012141142       7/2012

(Continued)

OTHER PUBLICATIONS

Bunville et al., Kinetics and Equilibria in the Acid Denaturation of Deoxyribonucleic Acids from Various Sources. Biopolymers, 3, 213-240, 1965.\*

(Continued)

*Primary Examiner* — Frank W Lu
(74) *Attorney, Agent, or Firm* — Jacobson Holman, PLLC.

(57) ABSTRACT

In a method and arrangement for detecting binding events of molecules, at least one second molecule covalently bound to a ligand, and optionally bonded to a third molecule bound to a ligand, forms a specific non-covalent fond with a first molecule immobilised on a bioactive surface by a covalent bond, and binding events between an analyte molecule and the second-molecule bound ligand are detected by an analytical measuring method, wherein the specific non-covalent (Continued)

Figure 3:
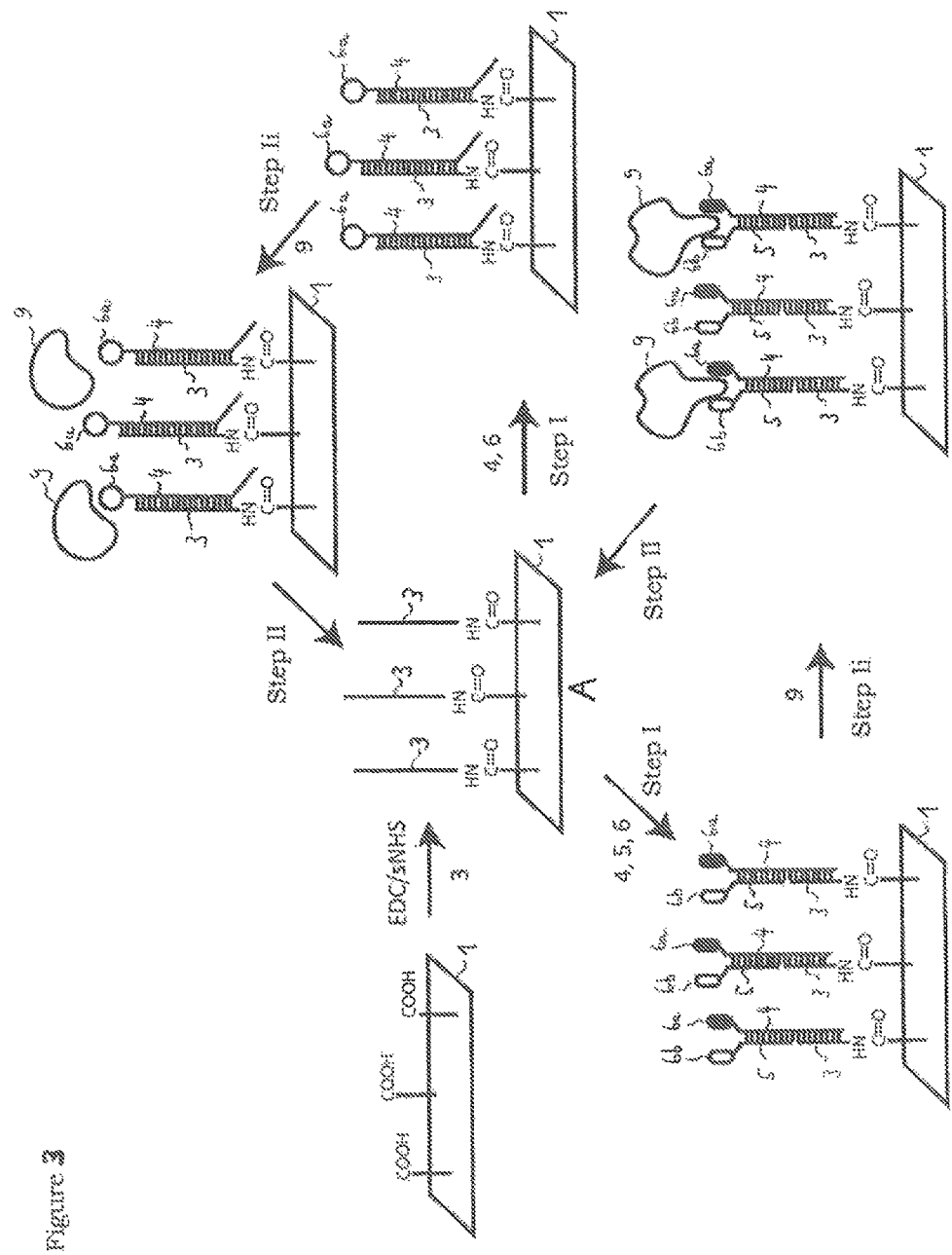

bond between the first and second molecules is breakable by supplying a buffer solution, and, hence, a specific ligand, or two, different specific ligands are made available on the bioactive surface in an easily reversible manner.

11 Claims, 4 Drawing Sheets

(56) References Cited

U.S. PATENT DOCUMENTS

| | | |
|---|---|---|
| 2004/0005582 A1 | 1/2004 | Shipwash |
| 2005/0009050 A1* | 1/2005 | Nadeau ............... C12Q 1/6804 435/6.18 |
| 2005/0014179 A1 | 1/2005 | Karlsson et al. |
| 2007/0087383 A1 | 4/2007 | Wu et al. |
| 2010/0029502 A1 | 2/2010 | Matysiak |
| 2011/0097740 A1 | 4/2011 | Paek et al. |
| 2011/0177509 A1* | 7/2011 | Goate ............... C12Q 1/6883 435/6.11 |

FOREIGN PATENT DOCUMENTS

| | | |
|---|---|---|
| WO | WO 01/79548 A2 | 10/2001 |
| WO | WO 03/059929 A1 | 7/2003 |
| WO | 2004/060350 | 7/2004 |
| WO | WO 2008/036802 A2 | 3/2008 |
| WO | WO 2008/100161 A9 | 8/2008 |

OTHER PUBLICATIONS

Does the pH influence the stability of double stranded DNA? from Biosyn.com. Printed on Jun. 23, 2019.*

Abramov et al., "HNA & ANA high-affinity arrays for detections of DNA & RNA single-base mismatches", Elsevier, Biosciences & Bioelectronics, vol. 23 (2008) pp. 1728-1732.

Tang et al., "DNA-directed assembly of protein microarrays", Frontiers in Bioscience, vol. 13, pp. 5755-5771, May 1, 2008.

Brandstetter et al., "A polymer-based DNA biochip platform for human papilloma virus genotyping", J. Virological Methods, vol. 163, pp. 40-48, (2010).

Wang et al., "Microarrays Assembled in Microfluidic Chips Fabricated From Poly(methyl methacrylate) for the Detection of Low-Abundant DNA Mutations", Anal Chem vol. 75 1130-40, 2005.

Hauser et al., Utilising the left-helical conformation of L-DNA for analysing different marker types on a single universal microarray platform, Nucleic Acids Research, Oct. 1, 2006, vol. 34, No. 18, pp. 5101-5111.

* cited by examiner

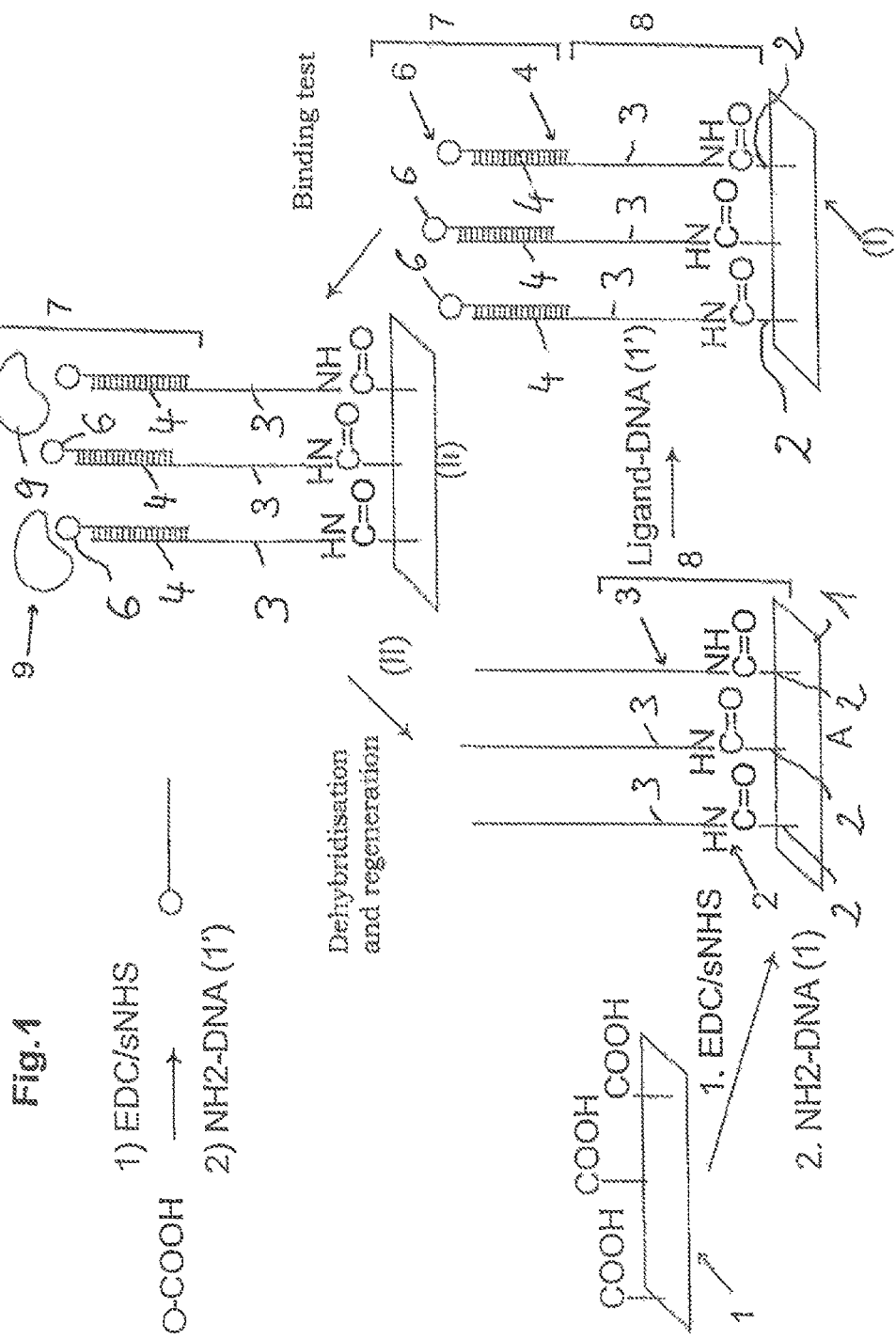

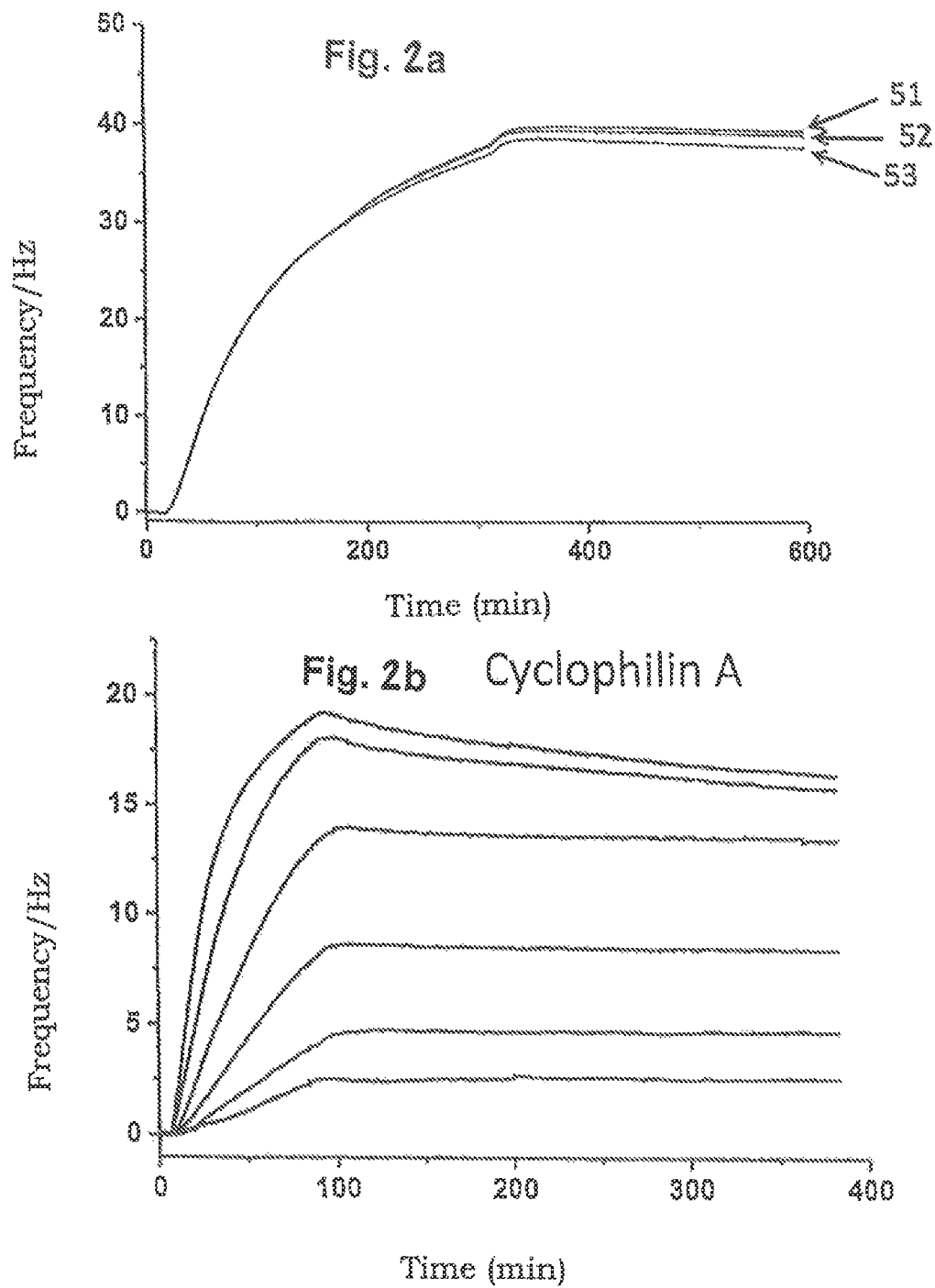

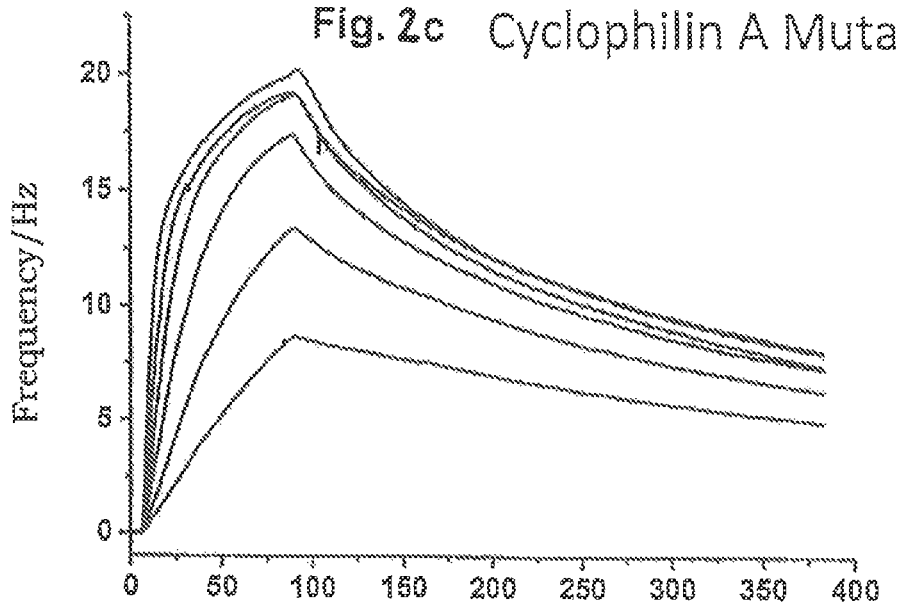
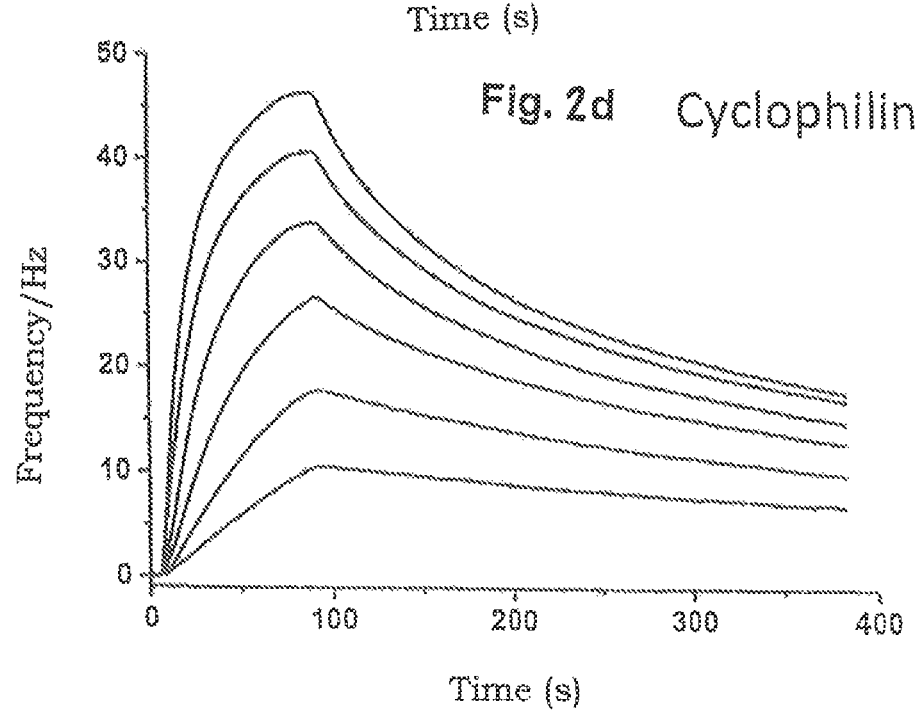

METHOD AND ARRANGEMENT FOR DETECTING BINDING EVENTS OF MOLECULES

The invention relates to a method and an arrangement for detecting binding events of molecules which are suitable in particular for high throughput applications.

Knowledge and understanding of binding events and interactions between biomolecules represents an essential field of work of biological, pharmaceutical and medical research. It is thereby the aim to track down possible binding partners and to characterise the signal paths thereof in order to be able to develop therapies or drugs with the knowledge obtained therefrom. Pharmaceutically relevant active substances are discovered for example by means of screening methods in which a large number of molecules or structures which are catalogued in libraries are tested against each other or against known target structures for the binding properties thereof. Hence from the large number of catalogued structures, for example those structures which bind to a pathogenic protein and consequently inhibit it can be determined. In order to detect such structures, the known target structures (targets) to be investigated are usually bonded covalently as stationary phase on the surface of a biochip, the thus immobilised targets then being brought in contact by flushing with a mobile phase, a liquid in which a large number of possible binding structures (molecules or molecule parts) are contained. During this contact, methods based for example on surface plasmon resonance (SPR) or on quartz crystal microbalance can determine the association and dissociation between the immobilised targets and the mobile structures (molecules or molecule parts).

It is obvious that it is necessary, in view of the large number of possible binding partners, to apply suitable high throughput methods with which the large number of possible binding combinations can be dealt with within a tolerable time. In particular because of the constant proliferation of substance libraries, pressure to achieve higher throughput rates is increasing. Because of the covalent bonding of the targets on the substrate or biochip side, it is however only possible under extreme conditions to achieve detachment of the thus immobilised targets. It is therefore necessary to prepare again a biochip for each target to be examined, in a laborious manner. In particular when implementing screenings with a plurality of targets in a high throughput, such biochips are therefore not suitable to a sufficient extent.

Methods are already known in which the binding between biotin and streptavidin is used for regeneration of a biochip. Streptavidin is thereby bonded covalently to the surface of the biochip. In a further step, biotinylated ligands bind on the immobilised streptavidin and form a stationary phase. Immobilised in the stationary phase, the ligands can be tested for their binding properties. Because of the high binding affinity of biotin to streptavidin which is equivalent to the binding strength of a covalent chemical bond, extreme conditions (for example high temperatures) are however necessary in order to effect a dissociation of the biotinylated ligands from the covalently bonded streptavidin. Although a detachment of the stationary phase formed with the biotinylated ligands is possible in principle, the extreme conditions lead to partial or complete denaturation of the streptavidin molecule so that a further immobilisation with biotinylated ligands on these streptavidin molecules is not possible or only with reduced binding strength.

It is therefore the object of the present invention to indicate possibilities for a reversible immobilisation of ligands.

According to the invention, this object is achieved with a method according to claim 1 and an arrangement according to claim 9.

Advantageous embodiments of the present invention can be deduced from the subordinate claims.

The inventive method comprises the features according to claim 1. In the case of the method according to the invention for detecting binding events of molecules on a bioactive surface, in a first step (I), to at least one first molecule which is immobilised on a bioactive surface by a covalent bond, at least one second molecule is bonded, with formation of at least one specific non-covalent bond.

The second molecule can be functionalised such that it is capable of binding/coupling to further third or fourth molecules. By contacting with a mobile phase comprising a target structure (i.e. an analyte) [step (Ii)], kinetic experiments (associations and dissociations) can then be implemented between the immobilised second, third or fourth molecules and the mobile target structures (analytes).

In a further step (II), the at least one specific non-covalent bond is broken again by supplying a buffer solution. There can thereby be understood by breaking the specific non-covalent bond, a dissociation of the second molecule from the first molecule, the covalently bonded first molecule remaining on the bioactive surface, and the second molecule including all molecules bonded thereon being removed from the surface. Subsequent to step (II), steps (I) and (II) can be repeated at least once again with the same second and/or third functionalised molecules and analytes or other second and/or third functionalised molecules and analytes.

There is intended to be understood by the bioactive surface, a surface which is suitable on the basis of its material properties and/or is functionalised or can be functionalised by chemical modification such that at least the first molecule can be immobilised thereon.

The bioactive surface can therefore also be configured in different geometric shapes. Thus the bioactive surface can be configured for example on biosensor chips or in bio-assays provided for this purpose or have a spherical form if it is configured on nanoparticles or beads. The bioactive surface can therefore be configured on the surface of different types of geometric structures.

During steps (I) and (II), the bioactive surface can always be covered with a buffer solution (running buffer). In step (I), a binding buffer which has a binding-favourable medium in particular for the molecule to be bonded can be used.

For breaking the specific non-covalent bond formed between the at least one first and the at least one second molecule, the bioactive surface can be contacted in step (H) with a buffer solution which has at least one molecule suitable for breaking the specific non-covalent bond, said molecule binding specifically to the second molecule and having a dissociation constant $K_D(I)$ relative to the second molecule which is less than a dissociation constant $K_D(II)$ of the at least one first molecule relative to the at least one second molecule.

As a result of the fact that the molecule supplied for the breaking has a dissociation constant $K_D(I)$ relative to the second molecule which is less than a dissociation constant $K_D(II)$ of the at least one first molecule relative to the at least one second molecule, the supplied molecule is also suitable for breaking the specific non-covalent bond since the molecule supplied for the breaking has a higher binding affinity to the second molecule than the first molecule to the second molecule, so that the first molecule is displaced by the second molecule. The breaking can be effected in a particularly gentle manner if the concentration of the molecule suitable for the breaking is increased successively or continuously during contacting with the buffer solution. At least a concentration of the molecule suitable for the breaking, which corresponds to the concentration of the first molecule immobilised on the bioactive surface, should thereby be achieved.

Alternatively, breaking of the specific non-covalent bond can also be achieved according to the invention by the bioactive surface being contacted with a buffer solution in step (II), which has a pH value of pH 1 to 4, preferably less than pH 3. Gentle breakage can hereby be achieved by slowly lowering the pH value, a pH value of 1 not being intended to be fallen below.

The specific non-covalent bonding of the at least one second molecule to the at least one first molecule can be regarded as immobilisation of a stationary phase formed from the at least one second molecule, which stationary phase can be detached in step (II), simply by changing the buffer system, whilst a lower phase which is formed from the at least one first molecule remains on the bioactive surface because of the covalent bonding, and the second molecule including all molecules bonded thereto are removed from the surface. The stationary phase formed with the at least one second molecule can therefore be regarded as temporary stationary phase, successive temporary stationary phases being able to have different properties because of different immobilisations/functionalisations.

Therefore the phase which is formed with the at least one first molecule and is suitable for chemically binding the stationary phase formed with the at least one second molecule can be understood as lower phase. However, also first molecules which are constructed in a complex manner and bonded covalently to the bioactive surface can be used as lower phase. These can be for example diamino linkers coupled to activated carboxyl groups which bond the first molecule covalently, the first molecule being intended to have a corresponding amino functionalisation. In addition, it is conceivable that the first molecule is immobilised in a solid or gel-like matrix on the bioactive surface, for example of a biosensor chip.

After detachment of the stationary phase formed with the at least one second molecule, again binding of a further stationary phase formed with the at least one second molecule can be effected again, subsequent to step (II).

Advantageously, the bioactive surface should be flushed with a prescribable volume flow of buffer solution in step (II), in order to be able specifically to remove detached second molecules and further molecules bonded thereto. The method is therefore suitable in particular for applications in throughflow cells in which a change in fluid flows can be achieved in a simple manner.

The method according to the invention is suitable in particular also for high throughput applications since a large quantity of successive loading and detaching of various second molecules, i.e. different temporary stationary phases, can be implemented without substantial interruptions.

In addition to the stationary phase formed with the second molecule, also further molecules can be supplied for immobilisation in step (I). Thus also binding of the at least one third, optionally of the at least one fourth molecule, can also be effected in step (I), in particular via cooperative binding to the at least one second molecule. Thus stationary phases with different properties can be obtained.

Preferably, a first molecule which has a dissociation constant $K_D(II)$ relative to the at least one second molecule which is greater than the dissociation constant $K_D(III)$ of the at least one second molecule relative to the at least one third or fourth molecule should thereby be used. As a result, it can be ensured that also a stationary phase formed from a plurality of third and fourth molecules can be detached reliably, in step (II), from the lower phase formed with the at least one first molecule, without the second, third and/or fourth molecules dissociating during elution, i.e. during breaking of the non-covalent specific bond (between the first and the second molecule) in step (II). Thus, complexes formed from the second, third and fourth molecules during the first step (I) can be detached and removed entirely from the lower phase.

Also a first molecule which comprises a first single-strand DNA (deoxyribonucleic acid)/RNA (ribonucleic acid) or molecules such as e.g. PNA (peptide nucleic acid) or LNA (locked nucleic acid) or consists thereof can also be used, to which first molecule at least one second molecule which comprises a second single-strand DNA/RNA or PNA or LNA molecules or consists thereof is bonded complementarily at least in regions. The stationary phase is thereby formed from the second DNA/RNA single strands or from the PNA or LNA molecules which hybridise or bind at least in regions to the immobilised first DNA, RNA, PNA or LNA, with formation of DNA/RNA double strands or PNA or LNA molecule complexes. In this case, a physiological buffer solution with a pH value of pH 6 to pH 8 should be used.

In the case where a first single-strand DNA or RNA is used as first molecule and a second single-strand DNA or RNA as second molecule, the second single-strand DNA or RNA hybridising as stationary phase at least in regions, complementarily to the immobilised covalently bonded first DNA or RNA, the bioactive surface should be contacted, in step (II), with a buffer solution which has a pH value of less than 3 in order to effect the detachment of the stationary phase. When using PNA or LNA as first and second molecules, the procedure can take place thereby in the same manner.

As a result of the pH value change during contacting with the buffer solution, the DNA/RNA molecules denature, the DNA/RNA double strands formed in step (I) dissociating into DNA/RNA single strands. The dissociated components, i.e. in particular the second DNA/RNA single strand can then be removed for example with the flow of buffer solution. For regeneration and repeated binding to the immobilised DNA/RNA single strands, a neutralisation buffer (e.g. phosphate buffer, pH 7.4) can be supplied, as a result of which a. pH value which corresponds to the initial pH value can be achieved in the region of the immobilised first molecules.

The third molecule used can have a ligand or consist thereof, the ligand having been bonded or being bonded preferably covalently to the third molecule, in particular, the third molecule comprises a (so-called second) ligand which is bonded chemically covalently to the third molecule. Particularly preferably, the first and/or second ligand is distributed on the entire bioactive surface, i.e. the bioactive surface is covered homogeneously with the first and/or second ligand. The first and second ligand can be different or identical. The ligand and/or second ligand can be selected from a group consisting of proteins, peptides, lipids, DNA, RNA, PNA, LNA, oligosaccharides and low-molecular compounds with a molecular mass of ≤20,000 Da, preferably ≤10,000 Da, particularly preferably ≤3,000 Da, in particular ≤900 Da, and also combinations thereof. In particular when using DNA/RNA as first and second molecule, the ligand can hybridise for example in the form of a gene probe (nucleotide sequence) on the immobilised DNA/RNA. The ligand can however also be coupled to the DNA/RNA in the form of a protein.

As already described above, further steps (Ii), in particular between steps (I) and (II), can be implemented, for example in order to detect ligand-analyte binding events, preferably by means of surface plasmon resonance spectroscopy (SPR), light interference measurement (LIM) and/or quartz crystal microbalances (QCM), without the binding stability of the stationary phase bonded to the lower phase thereby being influenced. The bioactive surface is preferably contacted with a solution comprising at least one specific, preferably only one specific, analyte molecule (e.g. a protein as analyte molecule). Subsequently, the binding event of the analyte molecule to the bioactive surface is determined by an analytical measurement. The ligand which is bonded to the at least one second molecule is hereby considered as binding partner for the molecule from the solution. If the third molecule likewise comprises a (so-called second) ligand, then this ligand also is considered as binding partner, the binding being particularly strong if both ligands take part in the binding to the analyte molecule. The first, second and/or third molecule serve merely as platform for the ligand/ligands and are not intended to take part in the binding to the analyte. Thus, with the method according to the invention, potential ligands can be offered for a known analyte specifically and in a reversible manner and binding events between analyte molecules and ligands can be measured. In particular during application with and on particles or beads, methods (PerkinElmer) based on ALPHA (amplified luminescent proximity homogeneous assay) can be used for detecting protein-protein interaction. In addition, the use of fluorescence-based particle sorting systems is conceivable, such as e.g. throughflow cytometry or FACS (fluorescence activated cell sorting) in which molecule bindings or molecule-molecule interactions can be detected by fluorescence/chemoluminescence. In this case, further steps/incubations, for example for marking with fluorescent dyes, may be necessary.

For formation of the lower phase, the bioactive surface formed on nanoparticles, beads, bioassays or biosensor chips can have activatable carboxyl groups to which further (first) molecules can be coupled.

The inventive arrangement comprises the features according to claim 9. The arrangement according to the invention for detecting binding events of molecules has at least one first molecule which is immobilised on a bioactive surface by a covalent bond. The arrangement according to the invention has, in addition, at least one second molecule which is bonded to the at least one first molecule by a specific non-covalent bond, the specific non-covalent bond being breakable.

The crucial advantage of the arrangement according to the invention resides in the fact that a temporary stationary phase formed with the second molecule can be immobilised and can be removed again according to demand so that the bioactive surface is available for binding further second molecules. Advantageously, the lower phase formed from the at least one first molecule is not affected in its binding properties by detachment of the temporary stationary phase and can therefore be almost completely restored without laborious preparation being required.

As already explained above, there is understood by the bioactive surface, a surface which is suitable on the basis of the material properties thereof and/or is functionalised or can be functionalised by chemical modification such that at least the first molecule can be immobilised covalently thereon. The arrangement according to the invention is therefore suitable in particular for biosensor chips, bioassays, nanoparticles, beads and bead beds (or moulded article beds) and in particular for throughflow cells.

The arrangement according to the invention or at least the bioactive surface should be wetted with a physiological buffer solution (pH neutral) which protects from drying out. The arrangement according to the invention can also be surrounded by a housing for this purpose.

To the at least one second molecule, preferably at least one third and/or fourth molecule (the fourth molecule concerning the analyte molecule) can be bonded, in particular via a cooperative bond. As a result, the stationary phase can have a large number of configuration shapes, for example an immobilisation of pairs of ligands and analytes which interact with each other.

Breaking the specific non-covalent bond formed between the at least one first molecule and the at least one second molecule can be achieved by contacting with a buffer solution which comprises at least one molecule suitable for breaking the specific non-covalent bond and which has a dissociation constant $K_D(I)$ relative to the second molecule which is less than a dissociation constant $K_D(II)$ of the at least one first molecule relative to the at least one second molecule.

The first molecule can have a dissociation constant $K_D(II)$ relative to the at least one second molecule which is greater than the dissociation constant $K_D(III)$ of the at least one second molecule relative to the at least one third or fourth molecule. As a result, a detaching capacity of a stationary phase formed with the at least one second and the third and/or fourth molecule can be ensured without the stationary phase itself dissociating. Complexes formed from the at least one second and the third and/or fourth molecule hence remain even after detachment of the stationary phase and are hence removed from the surface.

In a further advantageous embodiment of the arrangement according to the invention, the first molecule can also comprise at least one first single-strand DNA/RNA or PNA or LNA or be formed therefrom, to which a second molecule comprising a second single-strand DNA/RNA or PNA or LNA or consisting thereof is bonded complementarily at least in regions. In this case, the second DNA/RNA or PNA or LNA forms the detachable stationary phase, the specific non-covalent bonds formed between the first DNA/RNA or PNA or LNA and the second DNA/RNA or PNA or LNA being detachable during contacting with a buffer solution which has a pH value which is less than pH 3.

For determining binding events between ligands and analytes (target structures), the stationary phase can be flushed or contacted with a mobile liquid phase in which the analytes are present. In addition to the at least one second molecule, the at least one third molecule can have a ligand or consist thereof, the ligand being bonded preferably covalently to the third molecule. Particularly preferably, the first and/or second ligand is distributed on the entire bioactive surface, i.e. the bioactive surface is covered homogeneously with the first and/or second ligand. The ligands can concern for example proteins, peptides, lipids, DNA, PNA, LNA and/or RNA, oligosaccharides, low-molecular compounds (small molecules) with a molecular mass of ≤20,000 Da, preferably ≤10,000 Da, particularly preferably ≤3,000 Da, in particular ≤900 Da, and also combinations thereof. During flushing/contacting with the mobile phase, the analytes (target structures) contained therein interact with the immobilised ligands.

In a further embodiment, the lower phase of the arrangement according to the invention can have further covalently bonded molecules which are suitable for immobilisation of the first molecule or can have complexes formed from molecules. These molecules can concern molecules which have a carboxyl group.

The arrangement according to the invention is suitable in general for analytical detection of binding events of molecules (e.g. of ligands and specific analyte molecules immobilised on the arrangement), in particular for high throughput applications in throughflow cells and for measurements by means of surface-plasmon-resonance (SPR), light interference measurement (LIM) and/or via quartz crystal microbalances (QCM). With the arrangement, binding events of specific analyte molecules from a solution onto the bioactive surface of the arrangement can be detected selectively. The ligand which comprises at least one second molecule is hereby considered as binding partner for the analyte molecule from the solution. If the third molecule likewise has a ligand, this ligand is also considered as binding partner, the binding being particularly strong if both ligands take part in the binding to the analyte molecule. The first, second, and/or third molecule serve merely as a platform for the ligand/ligands are not intended to take part in binding to the analyte. Thus with the arrangement according to the invention, specifically and in a reversible manner, potential ligands for a known analyte can be offered and binding events between analyte molecules and ligands can be measured. For detection of molecule-molecule interactions, the arrangement according to the invention, in particular when applied with or on particles or beads, can be used also for measuring methods/detection methods which are based on the principle of fluorescence-activated particle sorting, such as e.g. FACS (Fluorescence activated cell sorting) throughflow cytometry. It is obvious that, in this case, suitable fluorescent markers (markings) are used which bind specifically to at least one molecule which is bonded or immobilised on the bioactive surface.

The arrangement according to the invention finds a further application in conjunction with ALPHA.

Subsequently, the present invention and the advantageous embodiments thereof are described with reference to embodiments given by way of example.

There are shown:

FIG. 1: a loading and regeneration of a biosensor chip,

FIG. 2a an example of a reversible hybridisation of DNA single strands (A'; A) with reference to a QCM signal diagram FIGS. 2b-2d example experiments for detecting binding events (association and dissociation) between immobilised and mobile molecules with reference to QCM signal diagrams FIG. 3 a schematic illustration of the method principle according to the invention with reference to a further embodiment.

FIG. 1 shows a loading and regeneration of a biosensor chip in which the biosensor chip in the initial state A has an immobilisation of covalently bonded DNA single strands 3 as first molecule. The DNA single strands 3 on the bioactive surface 1 are thereby immobilised covalently on covalently bonded complexes 2. A lower phase which is formed at least from the complexes 2 with the DNA single strands 3 bonded covalently thereto is characterised with the reference number 8. In step (I) of the method, the lower phase 8 is contacted with a buffer solution in which second DNA single strands 4 are contained as second molecule. The second DNA single strands 4 thereby have covalently coupled ligands 6. During the contacting, the second DNA single strands 4 hybridise complementarily, i.e. specifically non-covalently to the immobilised DNA single strands 3 with formation of DNA double strands. The region which forms the upper stationary phase is thereby represented with the reference number 7.

In method step (Ii), the stationary phase 7 is contacted by flushing with a mobile phase, structures 9 (analytes) present in the mobile phase being able to associate with the ligands 6. During method step (Ii), the association and dissociation can be determined for example my means of quartz crystal microbalances.

For regeneration (detaching of the temporary stationary phase, reference number 7), the bioactive surface 1 in step (II) is contacted with a buffer solution by flushing at a prescribable flow rate, the buffer solution initially having a pH value which is in the range of pH 8 to pH 6 and being reduced slowly, during the contacting, until achieving a pH value less than 3.

As a result of the pH value change during contacting with the buffer solution, the double strands formed from the DNA single strands 3 and 4 denature, the second DNA single strands 4 dissociating from the first immobilised DNA single strands 3. The stationary phase 7 is thereby detached and removed with the flow of the buffer solution. Finally, a neutralisation buffer or running buffer which has a physiological pH value in the range of pH 6 to pH 7 is supplied, the immobilised DNA single strands 3 being able to renature.

In FIG. 2a, a hybridisation of two DNA single strands (A'; A), as described above, can be understood with reference to a QCM signal diagram, DNA single strands A which are present in a mobile phase (hybridisation buffer) and have a conjugation with cyclosporine A (CsA) hybridise on immobilised DNA single strands A'. In order to detach the second molecule immobilised by the hybridisation, i.e. the CsA-conjugated DNA A, 2.5 mM HCl with which the surface of the sensor chip is flushed or incubated for 120 s can be used. As can be deduced in addition from the diagram of FIG. 2a, hybridisation cycles, i.e. repeated DNA couplings to the immobilised DNA single strands A' 51, 52 and 53, show corresponding QCM signals.

With FIGS. 2b to 2d, kinetic experiments for determining the binding processes (association and dissociation) between the immobilised CsA molecules and cyclophilin A (CypA, FIG. 2b) and also the variants cyclophilin A mutant (CypA mutant, FIG. 2c) and cyclophilin 40 (Cyp40, FIG. 2d), described in FIG. 2a, are illustrated with reference to QCM signal diagrams.

Firstly, the QCM chip described as in FIG. 2a and on which the CsA molecules coupled to DNA A are immobilised is washed with protein-binding buffer (10 mM HEPS, 150 mM NaCl, 0.05% Tween 20, 1 μm BSA (bovine serum albumin), pH 7.4), cyclophilin A (CypA, FIG. 2b), cyclophilin A mutant (CypA, mutant, FIG. 2c) and cyclophilin 40 (Cyp40, FIG. 2d) being thereby added in various concentrations to the protein-binding buffer respectively. The corresponding cyclophilin molecule concentrations are expressed in stronger QCM signals, as can be deduced from the diagrams of FIGS. 2b to 2d. The injections (contactings) of the various molecule concentrations of the cyclophilin A (CypA, FIG. 2b), cyclophilin A mutant (CypA mutant, FIG. 2c) and cyclophilin 40 (Cyp40, FIG. 2d) were effected respectively with a volume flow of 25 μl/min at 22° C. for an injection duration of 84 s.

FIG. 2b shows the binding and dissociation of CypA on the QCM sensor chip in the ninth hybridisation or dehybridisation cycle. CypA was thereby used in the following concentrations: 6.25 nM, 12.5 nM, 25 nM, 50 nM, 100 nM, and 200 nM. After measuring the QCM signal, cleaning of the sensor chip respectively was effected by flushing with 1% sodium lauryl sulphate buffer (SDS) for 120 s.

FIG. 2c shows the binding and dissociation of CypA mutant on the QCM sensor chip, the CypA mutant having been supplied in the concentrations 31.25 nM, 62.5 nM, 125 nM, 250 nM, 500 nM and 1,000 nM.

FIG. 2c shows the binding and dissociation of Cyp40 on the QCM sensor chip, the Cyp40 having been supplied in the concentrations 31.25 nM, 62.5 nM, 125 nM, 250 nM, 500 nM and 1,000 nM.

In none of the QCM sensor chips according to the invention used in FIGS. 2b to 2d could dehybridisation of the DNA double helix (A'; A) as a result of the Washing process with the 1% SDS buffer solution be established during implementation of the binding experiments (2b to 2d). Detachment or dehybridisation of the CsA-coupled DNA strand A can only be achieved by pH reduction.

FIG. 3 shows a schematic illustration of a method principle according to the invention for detecting binding events of molecules on a bioactive surface of a biosensor chip, the progress of the method being indicated with the arrows, in the initial state A, the bioactive surface 1 of the biosensor chip is covered completely by a binding buffer and has an immobilisation of at least a first molecule 3 which concerns single-strand DNA which is bonded chemically covalently to the chip 1. This chemically covalent immobilisation can be achieved for example by a chip being made to react with free carboxyl groups with single-strand DNA which has free amino groups ($NH_2$-ssDNA) in the presence of EDC/sNHS. Analogously, any ligand 6a, 6b which has a free carboxyl group can be made to react with an $NH_2$-ssDNA 4, 5 and EDC/sNHS. As a result, second molecules 4 and/or third molecules 5 according to the invention can be generated, which molecules have bonded chemically covalently to a ligand 6a, 6b.

in a step (I), firstly a second molecule 4 which presently concerns single-strand DNA is bonded (hybridisation) to the at least one first molecule 3, with formation of at least one specific non-covalent bond (hydrogen bridge bonds between the nucleotide bases). The second molecule 4 has a (e.g. chemically covalent) bond to a ligand 6a. In addition, also a third molecule 5 can be bonded to the second molecule 4 in step (I). The third molecule has a (e.g. chemically covalent) bond to a (so-called second) ligand 6b, the two ligands 6a, 6b being different in this example.

In method step (Ii), the molecules are contacted with ligands by flushing with a mobile phase, molecules 9 present in the mobile phase (e.g. a specific protein as analyte) being able to associate with ligands 6a, 6b. During method step (Ii), the association and dissociation between the immobilised ligands 6a, 6b and the structures 9 can be determined analytically, for example by means of surface plasmon resonance spectroscopy.

In step (II), the bioactive surface 1 is contacted (not shown) with a buffer solution having a pH value less than three by flushing with a prescribable volume flow. By means of the low pH value, the hybridisation of the single-strand DNAs is detached (dissociation) and the first molecule 3 immobilised chemically covalently on the surface 1 of the biochip remains in place, i.e. the biochip is regenerated and ready for renewed assembling with second and optionally third molecules. Consequently, the entire method is reversible so that the biochip can be used many times in succession for measurements.

Subsequent to step (II), the bioactive surface 1 can be rinsed with a running buffer (preferably phosphate buffer PBS with pH 7) in order to adjust the pH value of pH 3 to a neutral pH value.

The invention claimed is:

1. An arrangement for detecting binding events of molecules on a bioactive surface, comprising
    at least one first molecule immobilised on the bioactive surface by a covalent bond, the first molecule being selected from the group consisting of single-strand DNA, RNA, LNA and PNA,
    at least one second molecule bonded to the at least one first molecule by a specific non-covalent bond, the at least one second molecule being selected from the group consisting of single-strand DNA, RNA, LNA and PNA, and the second molecule being bonded chemically covalently to a ligand selected from the group consisting of lipids, PNA, LNA, and oligosaccharides,
    at least one third molecule bonded to the at least one second molecule via at least one specific non-covalent bond, the at least one third molecule being selected from the group consisting of single-strand DNA, RNA, LNA and PNA, and the at least one third molecule being bonded covalently to a second ligand,
the specific non-covalent bond between the first molecule and the second molecule being breakable by contacting the bioactive surface with a buffer solution capable of breaking specific non-covalent bonds among molecules, and the bioactive surface being suitable for analytical measurement of binding events using at least one of surface plasmon resonance spectroscopy (SPR), light interference measurement (LIM), and quartz crystal microbalances (QCM), wherein the bioactive surface is essentially dry.

2. The arrangement according to claim 1, wherein the first second ligand is selected from the group consisting of peptides, proteins, lipids, DNA, RNA, PNA, LNA, oligosaccharides, and low-molecular compounds with a molecular mass ≤20,000 Da.

3. The arrangement according to claim 1, wherein the first ligand and the second ligand are identical or different.

4. The arrangement according to claim 1, wherein at least one analyte molecule is bonded to the bioactive surface by interacting with the first ligand and the second ligand.

5. The arrangement according to claim 1, wherein the buffer solution has a pH value less than 3.

6. A method for molecules on a bioactive surface with an analyte molecule, comprising the steps of
    (i) providing the arrangement immobilized on the bioactive surface of claim 1,
    (ii) contacting a first buffer solution comprising the analyte molecule with arrangement immobilized on the bioactive surface and detecting binding events between the analyte molecule and the first ligand and the second ligand by an analytical measuring method, wherein the analytical measuring method is at least one of surface plasmon resonance spectroscopy (SPR), light interference measurement (LIM), and quartz crystal microbalances (QCM),
    (iii) contacting a second buffer solution with the bioactive surface after step (ii), wherein the second buffer is capable of breaking specific non-covalent bond among molecules such that the second molecule and the third molecule of the arrangement are removed from the surface, and
    (iv) repeating steps (i), (ii), and (iii) at least once.

7. The method according to claim 6, wherein the second ligand is selected from the group consisting of peptides, proteins, lipids, DNA, RNA, peptide nucleic acid (PNA), LNA, oligosaccharides, and low-molecular compounds with a molecular mass ≤20,000 Da.

8. The method according to claim 6, wherein the first ligand and the second ligand are identical or different.

9. The method according to claim 6, wherein the analyte molecule is selected from the group consisting of peptides, proteins, lipids, DNA, RNA, PNA, LNA, oligosaccharides, and low-molecular compounds with a molecular mass ≤20,000 Da.

10. The method according to claim 6, wherein the second buffer solution has a pH value less than 3.

11. The method according to claim 6, further comprising, after step (ii), contacting the bioactive surface with a neutralisation buffer having a pH value in the range from pH 6 to pH 8.

* * * * *